United States Patent [19]

Wegner et al.

[11] Patent Number: 4,676,234
[45] Date of Patent: Jun. 30, 1987

[54] MOISTURE-HARDENABLE BANDAGING MATERIALS

[75] Inventors: Christian Wegner, Cologne; Gottfried Schneider, Leverkusen; Hans-Uwe Lanzke, Dormagen; Wolfram Mayer, Bergisch Gladbach; Kuno Wagner, Leverkusen; Wulf von Bonin, Leverkusen; Ulrich von Gizycki, Leverkusen; Dietmar Schaepel, Cologne, all of Fed. Rep. of Germany

[73] Assignee: Bayer Aktiengesellschaft, Leverkusen, Fed. Rep. of Germany

[21] Appl. No.: 829,893

[22] Filed: Feb. 18, 1986

Related U.S. Application Data

[60] Continuation of Ser. No. 828,456, Oct. 23, 1984, and a continuation-in-part of Ser. No. 545,013, Oct. 24, 1983, Pat. No. 4,570,622, said Ser. No. 828,456, is a continuation of Ser. No. 553,009, Nov. 17, 1983, abandoned, which is a continuation of Ser. No. 299,536, Sep. 4, 1981, abandoned, said Ser. No. 545,013, is a division of Ser. No. 336,206, Dec. 31, 1981, Pat. No. 4,411,262, which is a continuation of Ser. No. 898,753, Apr. 21, 1978, abandoned, which is a continuation of Ser. No. 782,656, Mar. 30, 1977, abandoned, which is a continuation-in-part of Ser. No. 684,131, May 7, 1976, abandoned.

[30] Foreign Application Priority Data

Sep. 6, 1980 [DE] Fed. Rep. of Germany ....... 3033659

[51] Int. Cl.$^4$ ................................................ A61F 5/04
[52] U.S. Cl. ...................................................... 128/90
[58] Field of Search .............. 128/90, 89 R, 155, 156; 428/266

[56] References Cited

U.S. PATENT DOCUMENTS

| 3,630,194 | 12/1971 | Boardman | 128/90 |
| 4,411,262 | 10/1983 | von Bonin et al. | 128/90 |
| 4,570,622 | 2/1986 | von Bonin et al. | 128/90 |
| 4,572,171 | 2/1986 | Wegner et al. | 128/90 |

FOREIGN PATENT DOCUMENTS

| 2353212 | 4/1975 | Fed. Rep. of Germany . |
| 2357931 | 5/1975 | Fed. Rep. of Germany . |
| 1578895 | 11/1980 | United Kingdom . |

*Primary Examiner*—John D. Yasko
*Attorney, Agent, or Firm*—Gene Harsh; Lawrence S. Pope

[57] ABSTRACT

The invention relates to a self-hardening material for supporting bandages which is packaged with exclusion of moisture and consists of an air-permeable, flexible carrier material which is impregnated and/or coated with a compound possessing at least 2 NCO groups. The self-hardening material has a greatly improved shelf life by being stored substantially oxygen-free in an air-tight pack.

6 Claims, No Drawings

MOISTURE-HARDENABLE BANDAGING MATERIALS

This application is a continuation-in-part of Ser. No. 545,013, filed Oct. 24, 1983, now U.S. Pat. No. 4,570,622 which itself is a divisional of Ser. No. 336,206, filed Dec. 31, 1981, now U.S. Pat. No. 4,411,262 which is a continuation of Ser. No. 898,753, filed Apr. 21, 1978, now abandoned which is a continuation of Ser. No. 782,656, filed Mar. 30, 1977, now abandoned, which itself was a continuation-in-part of Ser. No. 684,131, filed May 7, 1976, now also abandoned.

This application is also a continuation of our pending application Ser. No. 828,456, filed Oct. 23, 1984, which itself is a continuation of Ser. No. 553,009, filed Nov. 17, 1983, now abandoned, which in turn is a continuation of Ser. No. 299,536, filed Sept. 4, 1981, also now abandoned.

The present invention relates to moisture-hardenable bandaging materials which exhibit improved shelf life. This is achieved by storing conventional self-hardening bandaging materials based on flexible carriers, impregnated and/or coated with polyisocyanates, under conditions of substantial exclusion of oxygen.

There has long been a need to replace plasterimpregnated bandage strips, as a stiffening bandaging material, by other products, since such plaster bandages are undesirably heavy, have a low air permeability, rapidly lose strength when moist, absorb and scatter X-rays and accordingly interfere with the diagnostic evaluation of X-ray photographs, and, because of their inadequate water resistance often cause skin irritations caused by growth of bacteria or fungi in the bandage.

There has therefore been no lack of attempts to provide bandaging materials which do not suffer from these disadvantages. Thus, for example, attempts have already been made to impregnate bandaging material with polymer solutions which harden in UV light and to harden the resulting bandage by irradiation with a UV lamp (Clinical Orthopaedics and Related Research 103, 109–117 [1974]).

The handling of UV sources which this requires is troublesome; furthermore, the UV light only reaches the upper layers of the bandage, so that hardening in deeper layers does not occur at all, or requires a longer time. A further serious disadvantage of this process is the fact that during hardening by UV irradiation, observation of the fracture by X-ray inspection is not possible.

The subject of DE-OS (German Published Specification) No. 2,125,243 is an orthopaedic bandage consisting of a flexible carrier which is impregnated with certain water-soluble vinyl monomers. Before application, the orthopaedic bandage is brought into contact with water in the presence of catalytic amounts of a polymerisation initiator. Preferably, the bandaging material should, for this purpose, be dipped in water at 49°–55° C.; temperatures below 43° C. should be avoided. In spite of these high temperatures which are unpleasant for the patient to be treated, the hardening times of such bandages are about half an hour or more.

The prior art also includes thermoplastic bandages which can be applied without soaking in water, harden in a relatively short time and "breathe". However, such thermoplastic bandages must also be applied hot. In doing so, it is necessary to work very rapidly so that the bandaging material does not harden even whilst it is being applied. In many cases it is necessary—as practical experiments have shown—to re-soften the already applied bandage by external application of heat (for example by means of hot air) in order to achieve adequate mechanical strength of the hardened material. The high temperatures in this context not only constitute a nuisance to the patient but of course also make the work of the doctor carrying out the treatment more difficult, since the doctor repeatedly has to put his hand into hot liquids when applying the bandaging material.

DT-OS (German Published Specification) 2,353,212 describes a stiffening bandaging material which consists of a flexible base material which has been treated with substances containing oxycarbonylisocyanate groups. This bandaging material of DT-OS (German Published Specification) No. 2,353,212 has however not been able to find acceptance in practice because, on the one hand, the production of the bandage strips encountered difficulties, due to the extreme reactivity of the oxycarbonylisocyanates, which could hardly be overcome, whilst on the other hand the strength of the supporting bandages produced with such bandage strips did not meet practical requirements.

Supporting bandages, based on polyisocyanate, which are suitable for practical requirements were first described in DE-AS (German Published Specification) No. 2,357,931. They are carrier materials which are impregnated and/or coated with a reactive one-component system, based on low-molecular and/or high-molecular compounds having free isocyanate groups, which hardens on access of moisture. In order to ensure sufficiently rapid hardening of the bandaging material, it is in general necessary to add, to the reactive one-component system, catalysts for the isocyanate/water reaction (for example tertiary amines). This, however, reduces the shelf life of the bandaging material even if moisture is completely excluded; the shelf life is between a few weeks and a few months, depending on the nature and amount of the catalyst used and of the isocyanate, and depending on the storage temperature.

A substantial improvement in this respect can be achieved if, according to the technical teaching of DE-AS (German Published Specification) No. 2,651,089, higher-molecular polyisocyanates (so-called NCO prepolymers) based on aromatic polyisocyanates, which contain tertiary nitrogen in a chemically incorporated form, are employed as impregnating agents for the bandaging materials. Surprisingly, bandage strips based on such an impregnating agent harden very rapidly (within about 5 to 15 minutes) after they have been brought into contact with water, but nevertheless have a shelf life of about 12 months at room temperature if moisture is excluded.

However, for certain practical requirements, even the shelf life of the self-hardening bandaging materials according to DE-AS (German Published Specification) No. 2,651,089 is not yet fully satisfactory. Thus, the maximum shelf life at 40° C. drops to about 3 months. After this time, due to very diverse crosslinking reactions, which have not been clarified in detail, the viscosity of the impregnating agent has risen so greatly, even if water is completely excluded, that the bandage strip can no longer be satisfactorily unrolled or applied, and an adequate bond between the layers of the hardened supporting bandage is no longer ensured.

Accordingly, the present invention sets itself the object of improving the known self-hardening polyisocyanate-based bandaging materials so that even on exposure to elevated temperatures the bandage strips remain capable of application after lengthy periods.

Surprisingly, it has proved possible to achieve this object in a simple manner by storing the bandage strips not only with exclusion of moisture but also with substantial or complete exclusion of atmospheric oxygen.

Accordingly, the subject of the present invention is a self-hardening material for support bandages which is packaged with exclusion of moisture and consists of an air-permeable, flexible carrier material which is impregnated and/or coated with a compound possessing at least 2 isocyanate groups, characterised in that the self-hardening material is stored substantially oxygen-free in an air-tight pack.

"Substantially oxygen-free" is to be understood, in the sense of the present invention, to mean that in the air-tight pack less than 0.5 ml, preferably less than 0.2 ml, particularly preferentially less than 0.05 ml of oxygen (expressed at 0° C. and 1 bar) is present per gram of the impregnating and/or coating agent containing isocyanate groups. It is to be regarded as surprising that a substantial increase in the shelf life (more than 3 years at 23° C.; about 10 months at 40° C.) can be achieved by such substantial exclusion of oxygen (commercial bandage strips contain, as an order of magnitude, about 2 ml of oxygen per gram of the compound possessing isocyanate groups).

As impregnating agents for the bandage strips according to the invention it is in principle possible to use any compound possessing two or more isocyanate groups (preferably with a mean NCO functionality of between about 2.2 and 3.5), such as are described in detail in, for example, DE-AS (German Published Specification) No. 2,357,931. The polyisocyanates can be employed as such or in the form of their reaction products with a less than equivalent amount of water or a low-molecular and/or high-molecular polyol.

Examples of suitable aliphatic polyisocyanates are hexamethylene diisocyanate, the biuret of hexamethylene diisocyanate and dodecane 1,12-diisocyanate; as cycloaliphatic polyisocyanates, hexahydro-1,3- and/or -1,4-phenylene diisocyanate, perhydro-2,4'- and/or -4,4'-diphenylmethane diisocyanate, 2,4- and/or 2,6-hexahydrotoluylene diisocyanate and 1-isocyanato-3,3,5-trimethyl-5-isocyanatomethyl-cyclohexane may be mentioned. However, according to the invention aromatic polyisocyanates are preferred, for example 2,4-diisocyanatotoluene, 2,6-diisocyanatotoluene, mixtures consisting of these isomers, 4,4'-diisocyanatodiphenylmethane, 2,4'-diisocyanatodiphenylmethane, mixtures consisting of these isomers and optionally also containing small amounts of 2,2'-diisocyanatodiphenylmethane, polyisocyanate mixtures such as are obtained by phosgenation of aniline/formaldehyde condensates and which in addition to 4,4'-,2,4'- and 2,2'-diisocyanatodiphenylmethane contain higher-nuclear polyisocyanates of the diphenylmethane series, 1,5-naphthylenediisocyanate, 4,4',4"-triphenylmethane triisocyanate, and 1,3- and 1,4-phenylene diisocyanate. According to the invention, diisocyanates of the diphenylmethane series are particularly preferred.

For chemical modification the polyisocyanates mentioned can, as already stated, be reacted with less than equivalent amounts of polyhydroxy compounds. Preferably, 1 equivalent of the polyhydroxy compound is reacted with about 2-15 equivalents of the polyisocyanate. Suitable polyhydroxy compounds are, in addition to low-molecular diols and triols, such as, for example, propylene glycol, diethylene glycol, glycerol and trimethylolpropane, compounds which contain 2-4, preferably 2 or 3, hydroxyl groups and have a molecular weight of between 400 and 5,000, preferably 800-3,000, for example polyacetals, polythioethers, polycarbonates, polyesteramides, polyesters and especially polyethers, as described in detail in DE-AS (German Published Specification) No. 2,357,931.

To accelerate the hardening reaction with water, activators which are in themselves known, such as, for example, organo-metallic catalysts or, preferably, tertiary amines of the type known from polyurethane chemistry (see, for example, the Kunststoff-Handbuch (Plastics Handbook), Volume VII, Vieweg-Höchtlen, Carl-Hanser-Verlag, Munich 1966) can be added to the impregnating agents mentioned. However, according to the invention it is preferred, in accordance with the technical teaching of DE-AS (German Published Specification) No. 2,651,089, to employ, as impregnating agents, NCO prepolymers, based on aromatic polyisocyanates, which already contain chemically incorporated tertiary nitrogen atoms. Preferably, these NCO prepolymers contain 5-30% by weight, especially 10-25% by weight, of aromatically bonded isocyanate groups and about 0.05-2.5% by weight, preferably 0.1-1.5% by weight, of tertiary amine nitrogen atoms. Steps are furthermore taken, by suitable choice of the starting materials for the preparation of the NCO prepolymers, to ensure that the prepolymers have a viscosity of about 5,000-50,000, especially 10,000-30,000, cP/25° C. The preparation of such NCO prepolymers is carried out in a manner which is in itself known, for example by reaction of excess amounts of aromatic polyisocyanates with compounds, which in addition to tertiary amine nitrogen, contain one or more primary or secondary amino groups or, preferably, hydroxyl groups.

Examples of suitable polyols containing tertiary amine nitrogen are: low-molecular polyols, containing tertiary nitrogen and free from ether groups, and having molecular weights in the range of 105-300, such as, for example, N-methyl-diethanolamine, N-ethyl-diethanolamine, N-methyl-dipropanolamine, triethanolamine or tripropanolamine; polyester-polyols containing tertiary nitrogen and having molecular weights in the range of 300-2,000, preferably 800-1,500, such as can be obtained by reacting polybasic acids with aminoalcohols of the type mentioned as examples above, optionally with simultaneous conjoint use of nitrogen-free polyhydric alcohols (suitable polybasic acids being, for example, adipic acid, phthalic acid or hexahydrophthalic acid, whilst examples of suitable nitrogen-free polyhydric alcohols for the preparation of the polyesters are ethylene glycol, tetramethylene glycol, hexamethylene glycol or trimethylolpropane; and polyetherpolyols, containing tertiary amine nitrogen, and having molecular weights in the range of 300-2,000, preferably 800-1,500, such as can be obtained in a manner known per se by alkoxylation of nitrogen-containing starter molecules (suitable nitrogen-containing starter molecules being, for example, the aminoalcohols mentioned as examples above or amines containing at least 2 N-H bonds, such as, for example, ethylenediamine, aniline or hexamethylenediamine, whilst suitable alkylene oxides for the preparation of the polyethers are, for example, ethylene oxide or propylene oxide, the propoxylation products of the stated nitrogen-containing starter molecules being particularly preferred).

Air-permeable, flexible sheet-like structures serve as the base material for the bandage strips according to the invention, and are impregnated and/or coated with the compounds, containing isocyanate groups, which have been mentioned by way of examples above. Examples of suitable base materials are textile sheet-like structures, for example gauze bandage strips, porous films or foams of natural or synthetic materials, for example polyurethane. Knitted fabrics, woven fabrics or non-wovens of natural or synthetic organic or inorganic fibre materials having a more or less resilient character are particularly suitable, examples being fibres of leather, cellulose, glass, polyamide, polyolefine, PVC, polyurethane, rubber, polyacrylate, metal, carbon, polyimide, wool or polyester. The carrier materials can be produced either from individual fibres or from fibre bundles, filaments, or film tapes. Preferred carrier materials for the bandaging material according to the invention are foam sheets, papers, glass fabrics, glass webs and woven fabrics, knitted fabrics or non-wovens, known per se, consisting of a single type, or a blend, or natural and/or synthetic fibres or filaments, for example wool, cotton, aromatic or aliphatic polyamides, polyimides, polyesters, polyacrylonitrile, PVC or polyolefines.

In the production of the bandage strips according to the invention, the stated carrier materials are subjected to an impregnating and/or coating process with the abovementioned compounds, containing isocyanate groups, in a manner known per se, for example by doctor-coating, impregnating and subsequent squeezing off on rolls or centrifuges, spraying or reverse-roll coating. The polyisocyanate can, in these processes, be employed either undiluted or in the form of a solution. If solutions are used, readily volatile solvents, such as, for example, methylene chloride, are preferably employed. Care is taken, through suitable choice of the weight per unit area (about 20–1,000), preferably 30–500 g/m$^2$, the mesh width of the flexible carrier and the amount of polyisocyanate applied (preferably 50–300% by weight. relative to untreated sheet-like structure) to ensure that the fibre materials are merely coated, but that voids are retained so as to ensure the requisite breathability.

If auxiliary solvents are also used, the impregnated carrier material is freed from these by, for example, a vacuum treatment. After the impregnation, the bandage strips according to the invention are stored in closed devices, in the absence of moisture. Preferably, the bandage strips according to the invention are stored in the form of rolls or in plated-down form, in plastic and/or metal, for example aluminium, containers, which are closed air-tight. Heat-sealed pouches of polyethylene-coated aluminium foils, or aluminium cans closed moisture-tight are particularly suitable in this context.

The substantial exclusion of oxygen, which is essential to the invention, can be achieved, for example, by pumping out the container. This pumping out can be effected either during the sealing process or by subsequent pumping out after the bandage strip has been introduced into the packaging container.

However, substantial exclusion of oxygen can also be achieved by storing the bandage strip in a dry protective gas atmosphere. Suitable protective gases are all materials which are gaseous under the storage conditions and do not react with the polyisocyanate, such as, for example, nitrogen, carbon dioxide, carbon monoxide, saturated and unsaturated hydrocarbons, halogenated hydrocarbons, noble gases and hydrogen. Nitrogen, carbon dioxide and helium are particularly suitable. Storage under a protective gas can equally be either in pouches which have been sealed air-tight or in air-tight dimensionally stable containers, for example cans.

The shelf lives of the bandage strips which, according to the invention, are kept under conditions of substantial exclusion of oxygen substantially exceed the shelf lives of moisture-hardenable polyurethane bandage strips of the prior art. This is true, as already mentioned, both at room temperature and at elevated temperatures. It is therefore not necessary to take special measures to avoid higher temperatures during storage of the bandage strips.

The bandage strips according to the invention can subsequently, at any desired point in time, be taken from the container and be impregnated with water. In applying the water-impregnated bandage strips according to the invention, the thickness of the supporting bandage depends on the particular medical requirements, but is in general between 3 and 10 mm. The bandage strips according to the invention can be employed both to produce supporting bandages by wrapping round the parts of the body to be supported, or also, if desired, in a plated-down form, for the production of shells or guides.

Before applying the bandaging material according to the invention, the part of the body which is to be supported is first covered with an air-permeable, nonimpregnated inner lining. Suitable materials for this inner lining are, for example, open-pore paper, non-wovens or textile bandaging materials. Preferably, the materials employed for the inner lining have only a limited hydrophilic character. Accordingly, for example, a non-woven polyester or polypropylene material is particularly suitable.

A bandage strip according to the invention, which has beforehand been saturated with water, is then wrapped over the part of the body which has been covered with the inner lining. The bandage strips according to the invention are saturated with water immediately prior to use, for example by dipping them in water.

The examples which follow serve to illustrate the invention.

EXAMPLE 1

A 12 cm wide gauze bandaging strip of bleached cotton, which is 4 m long, has a weight per unit area of 31 g/m$^2$ and a construction of 11 ends/cm in the lengthwise direction and 8 picks/cm in the crosswise direction of the woven strip is impregnated with 24 g of an NCO prepolymer consisting of (a) a phosgenation product of an aniline-formaldehyde condensate, containing 30% by weight of NCO groups and having a viscosity of 200 cP at 25° C. and (b) a trihydroxypolyether, obtained by propoxylation of triethanolamine and having an OH number of 146 and a viscosity of 1,200 cP/25° C., in the weight ration of a : b=3 : 1 (tert.-N: 0.3% by weight; 18.7% by weight of free NCO groups, viscosity 21,300 cP at 25° C.) on a roller impregnating unit, with very thorough exclusion of atmospheric moisture (dew point below −50° C.), and is then wound on a polyethylene core and sealed into a sealed-edge pouch of a polyester/aluminium/polyethylene triple laminate.

The shelf life of the bandage strip at 25° C. is 12 months. Thereafter, applying a fully satisfactory supporting bandage is no longer possible since the bandage strip has partially hardened and exhibits dry patches. Satisfactory unrolling of the bandage strip from the core and adequate bonding between the layers of the hardened supporting bandage are no longer achieved.

EXAMPLE 2

The bandaging material is produced and sealed into a pouch in accordance with Example 1. Thereafter, the air is extracted from the pouch by means of a cannula, and the pouch is closed again by sealing the point through which the cannula had been passed.

The shelf life of the bandage strip is substantially increased; even after a period of 24 months, it is still possible to apply a fully satisfactory supporting bandage.

EXAMPLE 3

The bandaging material is produced according to Example 1. However, it is sealed up on a tubularpouch machine, on which the sealing tools are located in a chamber which can periodically be closed and can be evacuated. The tubing, preformed by longitudinal sealing of the packaging material which comes vertically off a reel, is sealed at its lower end and the bandaging material is wrapped by introducing it from above. Above the material which has been introduced, the tube is then cut off and the chamber is closed and evacuated. The upper end of the tube, which is still open, is then also sealed. Thereafter air is admitted into the chamber, the latter is opened and the vacuum-packaged bandage strip is expelled. An example of such a machine is the ®Transwrap 125 H 100 with 1166 A evacuating unit, from Messrs. Hamac-Höller in Weerth/Netherlands.

EXAMPLE 4

The bandaging material is produced according to Example 1. However, it is sealed into the pouch in a dry nitrogen atmosphere. The shelf life of such a bandage strip is >24 months at 23° C.

EXAMPLE 5

The bandaging material is produced according to Example 1. However, it is sealed into the pouch in a dry carbon dioxide atmosphere. The shelf life of such a bandage strip is >24 months at 23° C.

We claim:

1. Self-hardening material for supporting bandages which is packaged with exclusion of moisture and consists of an air-permeable, flexible carrier material which is impregnated and/or coated with a compound possessing at least 2 NCO groups, characterised in that the self-hardening material is stored substantially oxygen-free in an air-tight pack.

2. Material according to claim 1, characterised in that the package contains less than 0.2 ml of oxygen, based on 0° C. and 1 bar, per gram of the compound containing NCO groups.

3. Material according to claim 1, characterised in that the package contains less than 0.05 ml of oxygen, based on 0° C. and 1 bar, per gram of the compound containing isocyanate groups.

4. Material according to claims 1-3, characterised in that the compound containing at least 2 NCO groups is a reaction product of 1 equivalent of a polyhydroxy compound with 2-15 equivalents of an aromatic polyisocyanate.

5. Material according to claims 4, characterised in that the polyhydroxy compound contains tertiary amine nitrogen.

6. Material according to claim 4 or 5, characterised in that the aromatic polyisocyanate is a diisocyanate of the diphenylmethane series.

* * * * *